United States Patent [19]

Ramzi et al.

[11] Patent Number: 4,855,457

[45] Date of Patent: Aug. 8, 1989

[54] CARBOXYLIC ANHYDRIDE PROCESS

[75] Inventors: Saleh Y. Ramzi, Neshanic Station; Israel E. Wachs, Bridgewater, both of N.J.

[73] Assignee: Exxon Research & Engineering Company, Florham Park, N.J.

[21] Appl. No.: 135,823

[22] Filed: Dec. 21, 1987

Related U.S. Application Data

[63] Continuation-in-part of Ser. No. 860,155, Nov. 12, 1985.

[51] Int. Cl.$^4$ .................................. C07D 307/89
[52] U.S. Cl. ................................ 549/239; 549/235; 549/236; 549/245; 549/248; 549/250; 549/253; 549/256; 549/257; 549/258; 549/259; 549/260
[58] Field of Search ............... 549/235, 236, 230, 245, 549/248, 250, 253, 256, 257, 258, 259, 260

[56] References Cited

U.S. PATENT DOCUMENTS 4,582,912 4/1986 Saleh et al. .................. 549/248 X

*Primary Examiner*—Richard L. Raymond
*Attorney, Agent, or Firm*—D. E. Furman; J. J. Mahon

[57] ABSTRACT

In accordance with the process of this invention, an improved catalyst for molecular oxidation of a hydrocarbon to form the corresponding carboxylic anhydrides is prepared by the steps of (a) forming a catalyst precursor by depositing on titanium dioxide solids in the anatase form at least a monolayer amount of at least one vanadium oxide source which is convertible to vanadium oxide upon calcining; (b) calcining the thus-formed catalyst precursor under conditions sufficient to convert the tantalum oxide source into the oxide form; (c) depositing upon the calcined catalyst precursor a catalytically effective amount of at least one vanadium oxide source which is convertible into vanadium oxide upon heating and at least one metal oxide source selected from the group consisting of oxides of Sb, Ga, Ge, In, T$_1$, Pb, Se, Te, P and Bi, which is convertible into the corresponding metal oxide upon heating and which is reactive with $V_2O_5$; and (d) calcining the vanadium and reactive metal-containing catalyst solids under conditions sufficient to form the corresponding vanadium oxide and reactive metal oxides.

The vanadium source and reactive metal source are employed in amounts sufficient to provide a molar ratio of vanadium to reactive metal of at least about 1:1, and preferably from about 1:1 to 6:1 gram atoms of vanadium per gram atom of reactive metal in the total catyalst, and wherein the combined weight percent of vanadium and the reactive metal (based on the oxides thereof), based on total catalyst weight is about 5 to 10 wt. %, and preferably from about 6 to 8 wt. %.

Preferably, the catalysts of the present invention are prepared by depositing on the calcined catalyst precursor, i.e. in step (c) above, sources of vanadium and reactive metal oxides in amounts sufficient to provide a molar ratio of vanadium deposited in step (c) to the reactive metal which is co-deposited therewith of at least about 1:1, and preferably from about 1:1 to about 4:1, gram atoms of vanadium per gram atom of the reactive metal; and wherein the combined weight percent, based on total catalyst weight, of vanadium added in step (c) and reactive metal co-deposited therewith (based on the oxides thereof) is from about 3 to about 9 wt. %, and more preferably from about 4 to about 6 wt. %.

21 Claims, 1 Drawing Sheet

CARBOXYLIC ANHYDRIDE PROCESS

CROSS-REFERENCE TO RELATED APPLICATION

This application is a continuation-in-part of Ser. No. 860,155 filed Nov. 12, 1985.

BACKGROUND OF THE INVENTION

This invention relates generally to the manufacture of carboxylic anhydrides, and more particularly to novel catalysts and methods for their use in manufacturing carboxylic anhydrides by molecular oxidation of hydrocarbon feedstocks, in particular the manufacture of phthalic anhydride by molecular oxidation of orthoxylene.

DESCRIPTION OF THE PRIOR ART

Aromatic carboxylic anhydrides are widely produced in large quantities through the molecular partial oxidation of hydrocarbon feedstocks, particularly phthalic anhydride from orthoxylene. The phthalic anhydride product is commercially useful for reactions with alcohols, such as oxo-alcohols to form the corresponding phthalic anhydride alcohol esters, which find use as plasticizers and lubricants.

Catalysts for the above partial oxidation, in which vanadium pentoxide is deposited on titania, are known in the art, for example, as disclosed in U.S. Pat. Nos. 3,464,930, 3,509,179, 3,909,457, 3,926,846 and 4,305,843 and British Patent Nos. 1,140,264 and 1,237,954.

See also S. Matsuda et al., *Applied Catalysis*, 8 (1983) 149–165, for discussion of titanium dioxide catalysts in general.

The art has sought to develop improved and promoted catalysts in order to enhance the activity and selectivity for the phthalic anhydride fraction. U.S. Pat. No. 4,052,418 (1977) to Standard Oil Company illustrates a promoted catalyst in which the vanadium pentoxide is admixed with an oxide of at least one of the group of boron, niobium, tantalum, antimony, tungsten and chromium (with or without one or more of the group of alkaline metals, zinc, cadmium, phosphorus, arsenic, copper, cerium, thorium, tin, manganese, iron and uranium) and uses supports such as silica, alumina, silicon carbide, boron phosphate, zirconia and alundum. The catalysts are prepared by digesting the vanadium pentoxide and the selected promoter oxide, such as antimony trioxide, in hydrochloric acid followed by drying at 120° C.

U.S. Pat. Nos. 4,076,731 and 4,075,231 disclose related Standard Oil Company oxide catalysts containing Sb oxide as an optional component.

Other disclosures of the use of Sb as a component of $V_2O_5$-$TiO_2$ anhydride catalysts can be found in U.S. Pat. Nos. 4,392,986; 4,397,768 and 4,435,521.

British Patent No. 1,186,126 (1978) to W. R. Grace discloses phthalic anhydride catalysts which are prepared by supporting on titania a mixture of alkaline metal pyrosulfate, vanadium oxide, together with at least one other metal oxide selected from the group of tellurium dioxide, antimony trioxide, niobium pentoxide, tin oxide, lead dioxide, manganese dioxide, germanium dioxide, and tantalum pentoxide. The catalysts are prepared to either form a solid solution of these additional metal oxides with vanadium oxide or are reacted with vanadium oxide to form a rutile structure. Catalyst preparations are exemplified in which the titanium dioxide support is dry blended with antimony trioxide, which is then sprayed with an aqueous solution of phosphorus pyrosulfate and vanadyl sulfate to saturate the solid phase followed by drying and calcining.

Canadian Patent No. 873,904 (1971) also to W. R. Grace, is drawn to the use of a four-component catalyst supported on titania containing vanadium pentoxide, potassium oxide, sulfur trioxide and antimony oxide. The patent discloses that $UO_2$, $Nb_2O_5$, $SnO_2$, $PbO_2$, $MnO_2$, $GeO_2$, $TaO_2$ and $TeO_2$ may be substituted for the antimony if desired. Other disclosed metal oxides are uranium oxide in addition to the oxides mentioned above in connection with British Patent No. 1,186,126. The patent's preferred catalyst preparation method requires dry blending of antimony trioxide (or other disclosed metal oxide) with a titanium dioxide support, and then contacting this mixture with the vanadium salt, potassium pyrosulfate and sulfur trioxide prior to calcining.

U.S. Pat. No. 3,862,960 to W. R. Grace relates to catalysts comprising vanadium oxide, potassium pyrosulfate and antimony oxide on a titania carrier promoted with cesium pyrosulfate. Again, a preferred catalyst preparation method is disclosed which requires intimately blending $TiO_2$ and $Sb_2O_3$ together, followed by depositing the V, K and/or Cs compounds, to form a solid which is then calcined. Sulfur dioxide (and, optionally, water vapor) is passed with the orthoxylene and oxygen feed over the catalyst to form phthalic anhydride.

U.S. Pat. No. 3,721,683 (1973) to Teijin Chemical Limited is directed to a process for preparing aromatic carboxylic anhydrides employing catalysts obtained by calcining a mixture of a vanadium compound, a chromium compound, and a promoter metal component selected from the group consisting of tin plus antimony, germanium, tin plus indium, niobimm, tantalum, gallium and zirconium, in specified atomic ratios of vanadium to chromium. The patent indicates that it is important that the mixture of the above components be calcined under controlled conditions. No $TiO_2$-containing catalyst is taught.

U.S. Pat. No. 4,012,338 to Tioxide Group Ltd. relates to a process for manufacturing a titanium dioxide carrier (e.g. for $V_2O_5$), preferably at least 50% of which is in the rutile form, and which contains from 0 to 200 parts of $Sb_2O_3$ per million parts of $TiO_2$ in addition to specified amounts of $Al_2O_3$, $SiO_2$, $P_2O_5$, $SO_3$, $K_2O$, ZnO, CaO, and $Na_2O$. U.S. Pat. No. 4,228,038 prepares a $TiO_2$-$V_2O_5$ catalyst containing 0.5 to 15% by weight $V_2O_5$, and indicates that the amount of $V_2O_5$ deposited (via the described method using vanadium oxytrichloride) should be at least equivalent to monolayer coverage.

U.S. Pat. No. 4,316,821 also to Tioxide Group, Ltd. relates to a method for production of a vanadium monolayer catalyst by contacting anatase titanium dioxide, having bound water residues on its surface and being substantially free of physisorbed water, with a decomposable vanadium compound dissolved in an organic solvent therefor, followed by removal of excess compound and solvent and decomposing the vanadium compound to form a monolayer of vanadium pentoxide.

U.S. Pat. No. 3,894,971 (1975) to BASF discloses a multi-layer supported catalyst which contains in the active material from 60 to 99 percent by weight of titanium dioxide and/or zirconium dioxide, from 1 to 40 percent by weight of vanadium pentoxide and up to 6 percent by weight of combined phosphorus, which contains from 0 to 0.3 percent by weight of phosphorus in the outer layer and more than 0.3 percent up to 6 percent by weight of phosphorus in the remaining catalytic material. Oxides of Al, Li, Nb, Sn, Sb, Hf, Cr, W, Mo and alkali and alkaline earth metals are also disclosed as being suitable in the catalytically active material. The percentage of V in the inner layer is preferably greater than in the outer layer. The catalyst is prepared by first depositing onto a support a vanadium/phosphorous compound in a slurry or paste with $TiO_2$ anatase, followed by depositing the second vanadium/phosphorous compound layer.

Other BASF catalysts are described in U.K. Patent No. 1,496,832 and U.S. Pat. Nos. 3,909,457; 3,565,829 and 3,684,741 in which $V_2O_5$-$TiO_2$ catalysts promoted with various alkali metal oxides, and other optional oxides of metals such as Al, Zr, Sb, As, Nb, Cr, Mo, W, Co, Ni, Fe, Mn, Sn, Ag, Cu, Ir and P, are prepared by depositing the $V_2O_5$ and metal promoters onto $TiO_2$ generally from a slurry, followed by calcining. U.S. Pat. Nos. 4,096,094 and 4,282,116 are also drawn to BASF $V_2O_5$-$TiO_2$ catalysts containing recited proportions of Rb, Cs, K and/or Sb.

U.S. Pat. No. 3,926,846 to Nippon Shokubai discloses $V_2O_5$-$TiO_2$ phthalic anhydride catalysts containing $Nb_2O_3$, $P_2O_5$, $K_2O$, $Cs_2O$, $ZrO_2$ and $Tl_2O$, and teaches that Sb is an undesired impurity at levels of greater than 0.05% by weight. U.K. Patent No. 1,409,377 and U.S. Pat. No. 3,870,655 to Nippon Shokubai similarly restrict the Sb content to not more than 1% by weight, based on the weight of $TiO_2$.

Japanese Patent Publication No. 71-006413 to Nippon Shokubai discloses catalysts containing $V_2O_5$, $TiO_2$, $K_2O$ and also 0 to 10 mol. % of $Sb_2O_3$ based on the $V_2O_5$ content. However, yields of only up to 94–98 wt. % phthalic anhydride are exemplified. U.S. Pat. No. 4,356,112 to Nippon Shokubai discloses catalysts containing 1–20 wt. % $V_2O_5$ and 99–80 wt. % porous $TiO_2$ anatase, and (based on the weight of $TiO_2 + V_2O_5$), 0.01 to 1 wt. % $Nb_2O_5$, 0.05 to 1.2 wt. % K, Cs, Rb or Tl oxide, 0.2 to 1.2 wt. % $P_2O_5$ and 0.5 to 10 wt. % $Sb_2O_3$. Antimony in the above compositions is indicated to provide improved heat stability, steam resistance and phthalic anhydride selectivity. Catalysts are prepared by depositing onto a carrier a slurry prepared by adding $TiO_2$ to an aqueous solution containing the selected V, Nb, P, Sb and Cs, Rb, K or Tl compounds, followed by calcining.

M. S. Wainwright et al., *Canadian Journal of Chemical Engineering*, 55, 557–564 (October 1977) investigated the influence of catalyst support material and product distribution for phthalic anhydride production via the oxidation of orthoxylene on vanadium pentoxide catalysts supported on titania and reports performance of W. R. Grace $V_2O_5$/$Sb_2O_3$ on $TiO_2$ catalyst.

Vanadium pentoxide monolayer catalysts have been studied and discussed in A. J. VanHengstum et al., *Applied Catalysis*, vol. 8, 369–382 (1983); M. Gasior et al., *Applied Catalysis*, vol. 10, 87–100 (1984); G. C. Bond et al., *Faraday Discussions of the Chemical Society*, vol. 72, 235–246 (1981) and G. C. Bond et al., *Journal of Catalysis*, vol. 77, 309–322 (1982).

Commonly-assigned U.S. Pat. No. 4,582,912, which is hereby incorporated by reference, discloses a phthalic anhydride catalyst prepared from sources of vanadium oxide, titanium oxide and the oxide of a promotor metal selected from Sb, Ga, Ge, In, Tl, Pb, Se, Te, P and Bi. The catalyst is prepared by a process of sequential deposition wherein at least a continuous monolayer amount of a vanadium oxide source is first deposited on $TiO_2$ anatase to form a catalyst precursor which is then calcined; and thereafter a vanadium oxide source and the oxide of at least one of the aforementioned reactive metals are deposited on the calcined catalyst precursor, the resulting catalyst solids then being calcined.

It is provided in the '912 patent that the thus-prepared catalyst contains generally from about 0.07 to 35 wt. % of V, preferably from about 0.2 to 20 wt. % V, and most preferably from about 3–10 wt. % V, calculated as $V_2O_5$; and from about 0.0007 to 35 wt. %, preferably from about 0.02 to 20 wt. %, and most preferably from about 0.1 to 10 wt. %, of the reactive metal, calculated as the corresponding metal oxide.

It is further recited that the ratio of vanadium to the reactive metal (e.g., antimony) is at least 1:1, preferably from about 1:1 to 100:1, more preferably from about 1.2:1 to 50:1, and most preferably from about 2:1 to 25:1, gram atoms of vanadium per gram atom of the reactive metal in the total catalyst.

In catalysts C, D, and E of the '912 patent, which exemplify the catalysts of the invention, the combined weight percent of $V_2O_5$ and $Sb_2O_3$, based on total catalyst weight, is about 11.5–11.6 wt. %, respectively. The mole ratio of vanadium to antimony in Catalysts C, D, and E is about 2.24:1 to 2.27:1 gram atoms of vanadium per gram atom of the reactive metal in the total catalyst. At 100 mol % orthoxylene conversion, phthalic anhydride yields of 112.6 wt. % (Catalyst D) and 112.3 wt. % (Catalyst C) are reported.

SUMMARY OF THE INVENTION

It has been surprisingly found that significantly improved phthalic anhydride yields are obtained employing catalysts prepared by a process of sequential deposition as described in commonly-assigned U.S. Pat. No. 4,582,912, wherein vanadium and a reactive metal are present in amounts described by certain weight percent and molar ranges.

The improved catalysts of the present invention are prepared by the steps of (a) forming a catalyst precursor by depositing on titanium dioxide solids in the anatase form at least a monolayer amount of at least one source of vanadium oxide, (b) calcining the thus-formed catalyst precursor under conditions sufficient to convert the vanadium oxide source into the oxide form, (c) depositing upon the calcined catalyst precursor a catalytically effective amount of at least one vanadium oxide source which is convertible into vanadium oxide upon heating and at least one metal oxide source selected from the group consisting of oxides of Sb, Ga, Ge, In, Tl, Pb, Se, Te, P and Bi, which is convertible into the corresponding metal oxide upon heating and which is reactive with $V_2O_5$, and (d) calcining the vanadium and reactive metal-containing catalyst solids under conditions sufficient to form the corresponding vanadium oxide and reactive metal oxides.

The catalysts of the present invention comprise vanadium and the reactive metal in a molar ratio of at least about 1:1, and preferably from about 1:1 to about 6:1, gram atoms of vanadium per gram atom of the reactive metal, and wherein the combined weight percent of vanadium and the reactive metal in the catalyst (based on the oxides thereof), is about 5 to about 10 wt. %, and preferably from about 6 to about 8 wt. %, based on total catalyst weight.

Preferably, the catalysts of the present invention are prepared by depositing on the calcined catalyst precursor, i.e. in step (c) of the above-described process, sources of vanadium and a reactive metal oxide in amounts sufficient to provide a molar ratio of vanadium deposited in step (c) to reactive metal of at least about 1:1, and preferably from about 1:1 to about 4:1, gram atoms of vanadium per gram atom of the reactive metal; and wherein the combined weight percent of vanadium and reactive metal co-deposited in step (c) (based on the oxides thereof) is from about 3 to about 9 wt. %, and more preferably from about 4 to about 6 wt. %, based on total catalyst weight.

Most preferably the catalysts of the present invention comprise vanadium and the reactive metal in a molar ratio of from about 1:1 to about 6:1, gram atoms of vanadium per gram atom of the reactive metal, and wherein the combined weight percent of vanadium and the reactive metal in the catalyst (based on the oxides thereof), is about 6–8 wt. %; and further, wherein the catalyst is prepared by co-depositing on the calcined catalyst precursor, vanadium and reactive metal oxide in amounts sufficient to provide a molar ratio of the vanadium to reactive metal co-deposited therewith of about 1:1 to 4:1, gram atoms of vanadium per gram atom of the reactive metal; and the combined weight percent of vanadium and reactive metal thus co-deposited (based on the oxides thereof) is from about 4 to about 6 wt. %, based on total catalyst weight.

Phthalic anhydride yields as high as 116.1 wt. % at 100 mol % orthoxylene conversion have been obtained employing the improved catalysts of the present invention.

Without being bound thereby, it is believed that the surface vanadia species in a phthalic anhydride catalyst in which a vanadium oxide source is deposited on an unmodified titanium dioxide anatase, followed by calcining, are present in two forms: a monolayer of vanadium oxide species, and a crystalline vanadium oxide species distributed thereon, as illustrated below:

The monolayer of vanadium species has been observed to have an inherent phthalic anhydride selectivity much greater than that of the crystalline vanadia species which is present above the monolayer. It has been found that the addition of a reactive metal oxide together with additional vanadium oxide source in defined amounts and under carefully controlled conditions to a vanadium oxide-titania catalyst results in a reaction of the vanadia crystalline species with the reactive metal oxide source to form crystallites which are believed to have a carboxylic anhydride selectivity greater than the vanadia crystallites themselves.

In addition, the observed marked yield enhancement achieved by the process and catalyst of this invention is only achieved when the vanadium oxide and reactive metal oxide are co-deposited onto a titania catalyst surface which has been first treated to form thereon a monolayer of vanadium oxide.

In contrast, if vanadium oxide and the reactive metal oxide, such as antimony trioxide, are co-deposited onto fresh titanium dioxide anatase, inferior catalyst performance results. It is believed that the titanium dioxide during such a preparation process may be incompletely covered with the desired vanadium monolayer species, and that the titanaum dioxide surface may either remain exposed, or may otherwise be adversely affected by the presence of antimony oxide surface species on the titania.

DETAILED DESCRIPTION OF THE INVENTION

Figure 1:
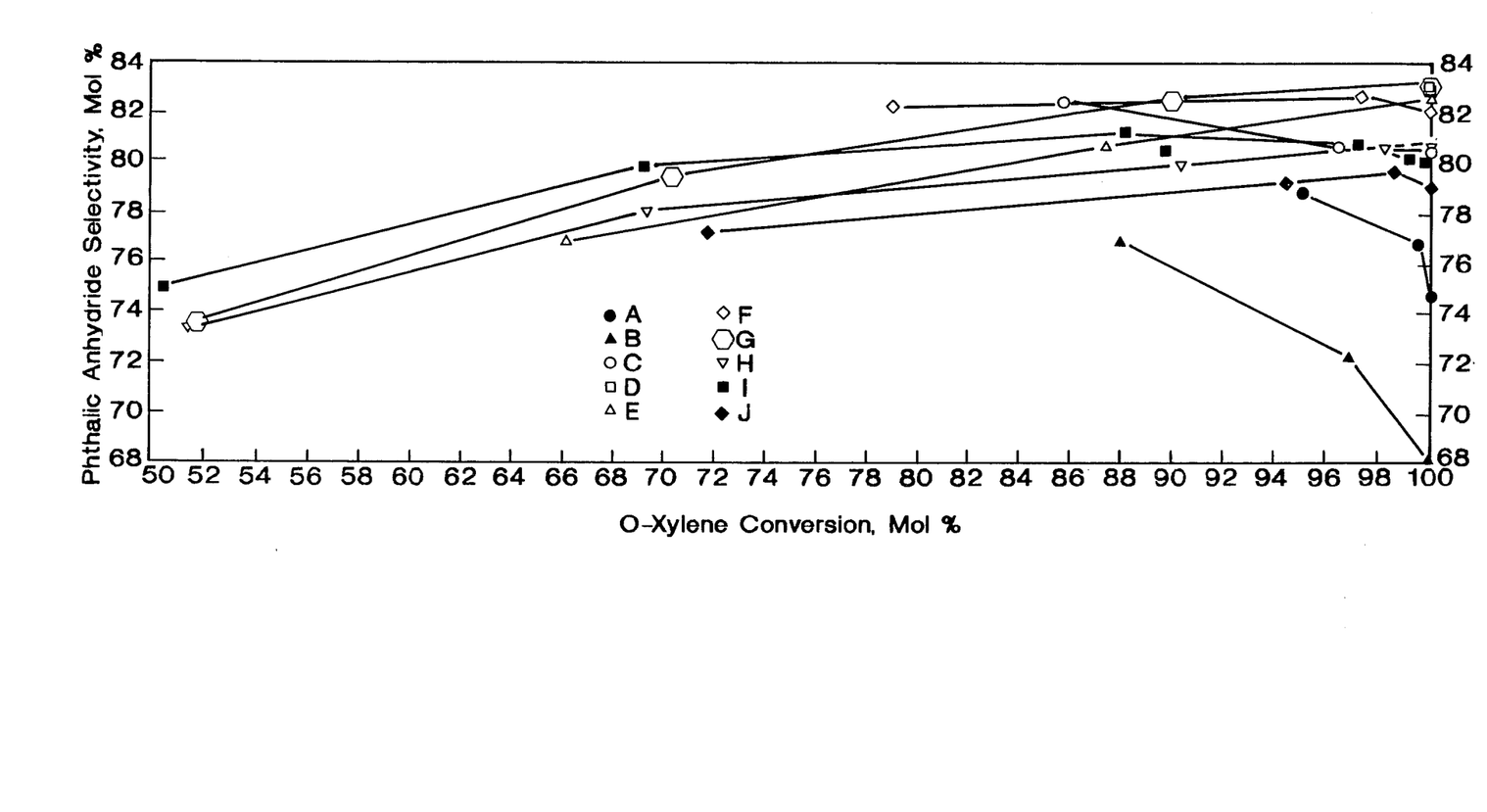
The FIGURE is a graphical plot of phthalic anhydride selectivities versus percent conversion of orthoxylene for a series of catalysts prepared and tested as described in Examples 1 and 2.

This invention relates to improved catalysts for the manufacture of carboxylic anhydrides by catalytic oxidation of hydrocarbons and relates more particularly to catalysts for producing aromatic carboxylic anhydrides such as phthalic anhydride and pyromellitic dianhydride by reacting a mixture of an oxygen-containing gas and an aromatic hydrocarbon (such as orthoxylene or naphthalene) in vapor phase in the presence of a novel catalyst therefor.

Catalyst Preparation

The improved catalyst of this invention is prepared by a four-step procedure, in which there is first deposited on titanium dioxide in the anatase form, vanadium oxide or at least one source of vanadium oxide, followed by calcining of this catalyst precursor to form a calcined catalyst precursor. The calcined catalyst precursor is then treated in a second deposition step with an additional amount of a vanadium oxide source admixed with at least one reactive metal oxide source, followed by calcining in a separate calcining step to obtain the desired improved anhydride catalyst.

Suitable sources of vanadium oxide are vanadium compounds and complexes which are convertible to the oxide upon heating to the calcination temperatures in the first calcination step. The valence of the vanadium oxide source may vary, although the pentavalent state is preferred. Suitable vanadium compounds include vanadium pentoxide but is preferably a vanadium compound such as an ammonium metavanadate, vanadyl sulfate, vanadyl halide (e.g., vanadyl chloride, vanadyl dichloride), vanadyl oxyhalide (e.g., vanadyl oxychloride), metavanadic acid, pyrovanatic acid, vanadium hydroxide, and vanadyl carboxylates such as formate, tartrate, salicylate and oxalate, which can then become vanadium oxide at the calcining temperature. The vanadium compounds most convenient for the catalyst preparation are $V_2O_5$ and vanadyl oxalate.

The selected vanadium oxide source can be dry mixed with the titanium dioxide or deposited on the titanium dioxide from solutions or suspensions of these vanadium oxide sources, for example, using aqueous or organic solvents. Illustrative organic solvents include formamide, diethyl acetamide, ammonium thiocyanate, molten urea or an alcohol. The solutions can be sprayed onto the titanium dioxide solids (for example, in a coating drum which has been preheated to from 150° to 450° C.) or impregnated thereon using conventional techniques.

If wet techniques are used to deposit the vanadium metal oxide source, the wetted solids can then be conveniently dried in air (or under an inert atmosphere such as nitrogen) to at least partially remove the solvent prior to calcination. Drying can be achieved by exposing the catalyst precursor to air at room temperature for a period of from about 1 to about 100 hours or by placing it in a forced hot air oven maintained at a temperature of less than about 180° C., typically between about 60° and about 150° C. for about 1 to about 16 hours. Alternatively, the precursor can be air dried at room temperature for between about 1 and about 48 hours and then placed in the forced hot air oven. Drying of the catalyst precursor preferably should be conducted at temperatures below which crystal phase transitions occur and until a level of nearly constant weight is achieved. Drying under reduced pressure at room or elevated temperature, as described above, can also be employed as a suitable alternative.

The thus-formed catalyst precursor is then, according to the process of this invention, calcined under conditions sufficient to convert the vanadium oxide source into the oxide form and to cause the vanadium oxide to be strongly attached to the surface of the titanium dioxide. Generally, a temperature of from about 100° to 750° C. will be sufficient, and temperatures of from 300° to 600° C. are preferred, and a time of calcination will range generally from 0.5 to 16 hours, with a time of from 1 to 5 hours being preferred. The precise temperature and time of calcination will depend upon the particular vanadium metal oxide source which has been selected for use, and should be such as to avoid crystal phase transformations of the $TiO_2$ anatase into another crystalline form, e.g., rutile.

The calcination can be performed, as is preferred, in air or in the presence of an $O_2$-containing gas. Although not essential, it is desirable to maintain a steady flow of the chosen atmosphere over the catalyst precursor surface during calcination. Flow rates typically will be sufficient to provide a contact time with the catalyst of about 1 to about 10, preferably from about 1 to about 5, and most preferably from about 1 to about 3 seconds. Thus, suitable flow rates or space velocities of the calcining atmosphere may be manipulated by one skilled in the art to achieve the desired contact time.

The titanium dioxide which is employed is preferably in the anatase form. Preferably at least about 25 wt. % (and most preferably from about 50–100 wt. %) of the titanium dioxide is in the anatase form. The titanium dioxide may be prepared by any conventional technique, for example the techniques described in R. J. H. Clark, "The Chemistry of Titanium and Vanadium", p. 267 (Elsevier Publishing Co., 1968).

The titanium oxide used in the catalyst of this invention is composed of substantially porous particles of a diameter of from about 0.4 to 0.7 micron and is preferably of a specific surface area of from 1 to 25 m²/g which are essentially aggregated masses of primary particles.

The particle diameter of the primary particles can be measured by a mercury penetration-type porosimeter. When using porous titanium oxide consisting of primary particles having a particle diameter in the range of 0.005 to 0.05 micron, the concentration of the slurry is 5 to 25% by weight, preferably 10 to 20% by weight. When using porous titanium oxide consisting of primary particles having a particle diameter of 0.05 to 0.4 micron, the slurry concentration is 10 to 40% by weight, preferably 15 to 25% by weight.

Depending upon the raw ore, the $TiO_2$ may include iron, zinc, aluminum, manganese, chromium, calcium, lead, silicon, etc. These incidental elements are not detrimental to the reaction if their total amount is less than 0.5% by weight based on $TiO_2$. Therefore, the $TiO_2$ can comprise pigment grade anatase, and no special purification procedure is required.

The resulting calcined titanium dioxide catalyst precursor will comprise from 0.07 to 35 wt. %, and preferably from about 0.2 to 20 wt. %, of vanadium oxide (calculated as $V_2O_5$). At least a monolayer of the vanadium oxide is required in order to achieve the improved results of this invention. In contrast, if the surface of the titanium dioxide is incompletely coated with the vanadium oxide (that is, if the $TiO_2$ has a discontinuous monolayer of $V_2O_5$ adsorbed thereon), inferior catalysts will result upon depositing thereon the additional amounts of vanadium and the reactive metal oxide, as will be hereinafter described. Therefore, the quantity of the vanadium metal oxide source which is contacted with the titanium dioxide solids should be at least sufficient to provide a continuous monolayer of $V_2O_5$ on the titanium dioxide solids, as calculated based on (1) the specific surface area of the $TiO_2$ (as conventionally determined by wet chemical analysis and BET surface area determinations), and (2) the cross-sectional area of $V_2O_5$ atoms relative to the surface density of the $TiO_2$.

The precise amount of the V oxide source which is required to form a continuous monolayer of $V_2O_5$ will depend on a variety of factors, such as the V oxide source selected (that is, the number of gram-moles of V per gram mole of the selected V oxide source), the specific internal surface area of the $TiO_2$, and other factors. As used herein, a "continuous monolayer amount" of $V_2O_5$ is defined to be the amount "$N_{min}$" as determined in the following expression (I):

$$N_{min} = (G) \times (A) \times (k) \qquad (I)$$

wherein "G" is the weight in grams of $TiO_2$ to be treated, "A" is the specific surface area in m2/gm (BET surface area) of the $TiO_2$ to be treated, "$N_{min}$" is the weight in grams of $V_2O_5$ to be employed and "k" is the number of grams of $V_2O_5$ required to form a continuous monolayer of $V_2O_5$ on 1 gram of $TiO_2$ having a specific surface area of 1 m²/gm. For $TiO_2$ having a specific surface area of from 1 to 25 m²gm, the value "K" in the above expression is 0.0007.

Therefore, expression (I) reduces to $$N_{min} = G \times A \times 0.0007 \qquad (II)$$

for $TiO_2$ having a specific surface area of from 1 to 25 m²/gm. As an example of the calculation, as defined herein, a "continuous monolayer amount" of $V_2O_5$ ($N_{min}$) for a 10 gram sample of $TiO_2$ having a specific surface area of 10 m²/gm will be (10)(10)(0.0007) or 0.07 gram of $V_2O_5$, and the selected V oxide source should be employed in an amount sufficient to provide at least 0.07 gram of $V_2O_5$, assuming complete conversion of the V oxide source to $V_2O_5$ on calcination. As defined herein, a "continuous mono-layer amount" of the V oxide source is the amount of the V oxide source which, upon complete conversion to $V_2O_5$, will provide $N_{min}$ grams of $V_2O_5$. More preferably, however, the V oxide source is employed as described herein for adsorption onto the $TiO_2$ in an amount sufficient to provide from $1 \times N_{min}$ to $40 \times N_{min}$, and most preferably from about $2 \times N_{min}$ to $18 \times N_{min}$, grams of $V_2O_5$, wherein $N_{min}$ is calculated as described above.

Of course, not every $TiO_2$ particle need be individually treated to form thereon a continuous $V_2O_5$ monolayer, and it can be understood that at least a majority (and most usually at least 90%) of the $TiO_2$ particles will be characterized by a continuous $V_2O_5$ monolayer when the $TiO_2$ sample is treated as described herein, particularly when using solution impregnation methods.

The presence of more than a monolayer of $V_2O_5$ can be observed by examining the $TiO_2$ catalyst surface for evidence of $V_2O_5$ crystallites which are believed to comprise the $V_2O_5$ species which forms when $V_2O_5$ is used in excess of the $V_2O_5$ monolayer amount. Such a surface examination for $V_2O_5$ crystallites can be conducted using Laser Raman Spectroscopy, as described in F. Roozeboom et al., *J. Phys. Chem.*, vol. 84, p. 2783, (1980).

The intermediate calcining step, in preparing the catalyst precursor, is believed to be necessary in order to cause the $V_2O_5$ to form the necessary bond with the $TiO_2$ surface. It is believed that the selected V oxide source is adsorbed (physically or both physically and chemically) onto the surface of the $TiO_2$ and that the calcining step converts the V source to the oxide (e.g., $V_2O_5$) which is chemically adsorbed on the $TiO_2$ surface.

The resulting calcined catalyst precursor solids are then treated in a separate step to co-deposit thereon an additional quantity of a source of vanadium oxide and a reactive metal oxide of at least one metal selected from the group consisting of Sb, Ga, Ge, In, Tl, Pb, Bi, P, Te, Se and mixtures thereof, followed by calcining in a separate step. Preferably, the metal of the reactive metal oxide source comprises at least one member selected from the group consisting of Sb, Tl, Pb, Bi and P. Antimony is an especially preferred metal associated with the reactive metal oxide source.

Any of the aforementioned vanadium compounds and complexes can be used. Thus, the vanadium metal oxide source may be vanadium pentoxide but is preferably a vanadium compound such as an ammonium metavanadate, vanadyl sulfate, vanadyl halide (e.g., vanadyl chloride), vanadyl dichloride), vanadyl oxyhalide (e.g., vanadyl oxychloride) metavanadic acid, pyrovanatic acid, vanadium hydroxide, and vanadyl carboxylates such as formate, tartrate, salicylate and oxalate, which can then become vanadium oxide at the calcining temperature. The vanadium compounds most convenient for the catalyst preparation are $V_2O_5$ and vanadyl oxalate.

The reactive metal oxide source can comprise metal compounds and complexes which are convertible to the metal oxide upon heating to the calcination temperatures employed in the second calcination step (described below). Preferred metal oxide sources are the metal oxides themselves and oxygen-containing compounds and complexes of such metals. Illustrative of such reactive metal oxide sources are the oxides, halides, phosphates, carbonates, oxyhalides, sulfates, alkoxides (e.g., $C_2-C_6$ alkoxides, such as ethoxide, propoxide, butoxide, pentoxide, etc.), nitrate, hydroxides, carboxylates (e.g., acetate, formate, tartrate, salicylate, and oxalate) and the like. Examples of such reactive metal oxide sources are $SbBr_3$, $SbCl_5$, $Sb_2O_3$, $SbH_3$, $SbI_5$, $SbOCl$, $Sb_2Se_3$, $Sb_2(SO_4)_3$, $Sb_2S_5$, $Sb_2S_3$, $Sb_2Te_3$, $Bi(O_2CCH_3)_2$, $BiAsO_4$, $BiBr_3$, $Bi_2O_2CO_3$, $BiCl_4$, $Bi(OH)_3$, $BiI_3$, $Bi(MoO_4)_3$, $Bi(NO_3)_3$, $BiO$, $Bi_2O_5$, $Bi_2O_3$, $BiOCl$, $BiPO_4$, $Bi_2TeO_6$, $Pb(O_2CCH_3)_2$, $Pb_2Sb_2O_7$, $Pb_3(AsO_4)_2$, $Pb_2As_2O_7$, $Pb(BO_2)_2$, $PbBr_2$, $PbCl_2$, $PbCrO_4$, $PbF_2$, $PbMoO_4$, $PbO$, $Pb_2O_3$, $Pb_2O$, $PbCl_2 \cdot 2PbO$, $PbSO_4$, $PbTiO_3$, $Ga(O_2CCH_2CH_3)_3$, $GaBr_3$, $GaCl_2$, $Ga_2O_3$, $Ga_2O$, $GaOCl$, $Ga_2(SO_4)_3$, $GaTe$, $Ga_2Te_3$, $GeBr_2$, $GeCl_4$, $GeO$, $GeO_2$, $GeSe_2$, $GeS_2$, $GeS$, $InSb$, $InAs$, $InBr_2$, $InBr_3$, $InCl$, $InI$, $In(NO_3)_3$ $In_2O$, $In_2O_3$, $InTe$, $In_2Se_3$, $In_2Te_3$, $Tl(O_2CCH_3)$, $TlBr$, $Tl_2CO_3$, $TlCl$, $Tl_2CrO_4$, $TlF$, $Tl_2MoO_4$, $TlNO_3$, $Tl_2O$, $Tl_2O_3$, $Tl_3PO_4$, $Tl_2SeO_4$, $PBr_5$, $PBr_3$, $PCl_5$, $PhdO_5$, $P_2O_3$, $P_2O_4$, $H_3PO_3$, $POBr_3$, $P_2O_3C_4$, $P_4O_6S_4$, $P_2Se_5$, $P_4Se_3$, $P(SCN)_3$, $TeBr_2$, $TeBr_4$, $Te(OC_2H_5)_4$, $Te(OCH_3)_4$, $TeO_2$, $TeO$, $TeO_3$, $TeS_2$, $TeSO_3$, $SeBrCl_3$, $SeO_2$, $SeO_3$, $SeOBr_2$, $SeOCl_2$, $SeSO_3Cl_4$, $SeSO_3$ and the like. Preferably, the selected reactive metal oxide source will be characterized by a Tamman temperature ($T_T$) of less than about 575° C., and more preferably less than about 525° C. (wherein $$T_T = \frac{T_M + 273}{2} - 273$$

in which $T_M$ is the melting point in °C. of the reactive metal oxide source), to promote mobility of the reactive metal oxide source on the surface of the solids during calcination in the catalyst preparation procedures. A discussion of Tamman temperature can be found in A. W. Adamson, *Physical Chemistry of Surfaces*, 3rd Ed., p. 250 (John Wiley & Sons, N.Y.) (1976). Examples of preferred reactive metal oxide sources are the oxides, phosphates, carbonates, sulfates, alkoxides, oxy halides, hydroxides, nitrates, carboxylates and the like. Especially preferred are the oxides, hydroxides, oxyhalides (particularly Br and Cl), alkoxides of 2 to 6 carbon atoms in each alkoxide moiety and carboxylates of 1 to 6 carbon atoms in each carboxylate moiety. Illustrative of such especially preferred metal oxide sources are $Sb_2O_3$, $SbOCl$, $Bi(O_2CCH_3)_2$, $Bi(OH)_3$, $BiO$, $Bi_2O_5$, $Bi_2O_3$, $BiOCl$, $Bi_2TeO_6$, $Pb(O_2CCH_3)_2$, $PbO$, $Pb_2O_3$, $Pb_2O$, $Ga_2O$, $GeO$, $GaOCl$, $In_2O$, $In_2O_3$, $Tl(O_2CCH_3)$, $Tl_2O$, $Tl_2O_3$, $Tl_2SeO_4$, $P_2O_5$, $P_2O_3$, $P_2O_4$, $H_3PO_3$, $Te(OC_2H_5)_4$, $Te(OCH_3)_4$, $TeO_2$, $TeO$, $TeO_3$, $SeO_2$, $SeO_3$, $SeOBr_2$, $SeOCl_2$.

The selected vanadium oxide and reactive metal oxide sources can be deposited on the calcined catalyst precursor from solutions or suspensions of the vanadium oxide and reactive metal oxide sources, for example using aqueous or organic solvents. Illustrative organic solvents include formamide, diethyl/acetamide, ammonium thiocyanate, molten urea or an alcohol. The solutions can be sprayed onto the calcined catalyst precursor solids (for example in a coating drum which has been preheated to from 150° to 450° C.) or impregnated thereon using conventional techniques.

If wet techniques are used, the wetted solids can then be dried in air or under an inert atmosphere (such as nitrogen) as described previously, conveniently at a temperature of from 50° to 200° C., followed by calcining for activation of the catalyst at a temperature of from 100° to 750° C., preferably 300° to 600° C. and for about 0.5 to 16 hours, preferably 1 to 5 hours. The precise conditions of calcining will vary depending upon the vanadium oxide source which is employed, and should be sufficient to convert the vanadium and reactive metal oxide compounds into the vanadium oxide (if non-oxide sources are employed). Again, the conditions of calcining should be such as to avoid crystal phase transformations of the $TiO_2$ anatase into another crystalline form, e.g. rutile.

The total grams of the selected V oxide source (calculated as its $V_2O_5$ equivalent weight) thus deposited on the final catalyst solids will preferably comprise at least about $1.7xN_{min}$, and more preferably from about $2.5xN_{min}$ to $40xN_{min}$, (wherein Nmin is calculated as in expression (II)). (Greater than $40xN_{min}$ can be used if desired, but generally provides no pronounced further benefit.)

The quantity of the reactive metal oxide source can vary but will preferably be sufficient to provide sufficient metal oxide to form the complex oxide $VM_xO_y$ (wherein "M" is the reactive metal, "x" is from 0 to 1, and "y" is sufficient to provide the gram atoms of oxygen necessary to satisfy the valences of V and M) during calcination in the second such calcination step.

The thus-prepared catalyst will contain generally from about 0.07 to 35 wt. % of V, preferably from about 0.2 to 20 wt. % V, and most preferably from about 3-10 wt. % V, calculated as $V_2O_5$, and from about 0.0007 to 35 wt. %, preferably from about 0.02 to 20 wt. %, and most preferably from about 0.1 to 10 wt. %, of the reactive metal calculated as the corresponding metal oxide.

The catalysts of the present invention comprise vanadium and the reactive metal in a molar ratio of at least about 1:1, and preferably from about 1:1 to about 6:1, gram atoms of vanadium per gram atom of the reactive metal, and wherein the combined weight percent of vanadium and the reactive metal in the catalyst (based on the oxides thereof), is about 5 to about 10 wt. %, and preferably from about 6 to about 8 wt. %, based on total catalyst weight.

Preferably, the catalysts of the present invention are prepared by co-depositing on the calcined catalyst precursor, sources of vanadium and reactive metal oxides in amounts sufficient to provide a molar ratio of vanadium co-deposited with the reactive metal of at least about 1:1, and preferably from about 1:1 to about 4:1, gram atoms of vanadium per gram atom of the reactive metal; and wherein the combined weight percent of the co-deposited vanadium and reactive metal (based on the oxides thereof) is from about 3 to about 9 wt. %, and more preferably from about 4 to about 6 wt. %, based on total catalyst weight.

Most preferably the catalysts of the present invention comprise vanadium and the reactive metal in a molar ratio of from about 1:1 to about 6:1, gram atoms of vanadium per gram atom of the reactive metal, and wherein the combined weight percent of vanadium and the reactive metal in the catalyst (based on the oxides thereof), is about 6-8 wt. %; and further, wherein the catalyst is prepared by co-depositing on the calcined catalyst precursor, vanadium and reactive metal oxide in amounts sufficient to provide a molar ratio of the vanadium to reactive metal co-deposited therewith of about 1:1 to 4:1, gram atoms of vanadium per gram atom of the reactive metal; and the combined weight percent of vanadium and reactive metal thus co-deposited (based on the oxides thereof) is from about 4 to about 6 wt. %, based on total catalyst weight.

The surface area of the activated unsupported catalyst can vary typically from about 1 to about 25 $m^2/g$.

Surface areas herein are determined by the BET method, the general procedures and theory for which are disclosed in H. Brunaur, P. Emmett and E. Teller, *J. of Am. Chem. Soc.* vol. 60, p. 309 (1938).

The catalyst can further comprise effective amounts of promoter metal oxides selected from the group consisting of niobium, magnesium, calcium, scandium, yttrium, lanthanum, uranium, cerium, chromium, manganese, iron, cobalt, nickel, copper, zinc, aluminum, silicon, tin, tantalum, hafnium, zirconium, alkali metals (Cs, Rb, K, Na, Li) and mixtures thereof. The promoters and/or activators are readily introduced into the catalyst during deposition of vanadium and the reactive metal oxide sources on the catalyst precursor by admixture with the vanadium and reactive metal compounds.

Typical compounds of zinc (illustrative of activators as a class) are metallic zinc, zinc oxide, zinc chloride, zinc bromide, zinc iodide, zinc formate, zinc nitrate or zinc acetate. Generally, phosphorus compounds are used which have as the cation an ion which is more volatile than the phosphate anion. Various compounds may be used, such as metaphosphoric acid, triphosphoric acid, pyrophosphoric acid, orthophosphoric acid, phosphorus pentoxide, phosphorus oxyiodide, ethyl phosphate, methyl phosphate, amine phosphate, phosphorus pentachloride, phosphorus trichloride, phosphorus oxybromide, and the like. The alkali metal may suitably be introduced by employing alkali metal compounds such as alkali metal salts with examples being lithium acetate, lithium bromide, lithium carbonate, lithium chloride, lithium hydroxide, lithium iodide, lithium oxide, lithium sulfate, lithium orthophosphate, lithium metavanadate, potassium sulfate, potassium chloride, potassium hydroxide, sodium chloride, sodium hydroxide, rubidium nitrate, cesium chloride and the like. Mixtures of two or more alkali metal compounds may be used, such as a mixture of lithium hydroxide and sodium chloride or a mixture of lithium chloride and potassium chloride. The preferred alkali metal elements are lithium, sodium and potassium, and mixtures thereof, with lithium being particularly preferred. The alkali metal compound will preferably be an alkali metal compound which either has a phosphate anion as the anion, that is a compound such as lithium phosphate, or a compound which has an anion which is more volatile than the phosphate anion.

These promoter metal oxides (or metal compounds which are sources for such oxides under calcination conditions) can be generally added to the catalyst solids by depositing on the calcined catalyst precursor with the vanadium. The amount of such promoter metal oxides which is employed in the catalyst can vary widely and will generally comprise from about 0.05 to 20 wt. % of the finally calcined catalyst, calculated as the corresponding promoter metal oxide. This will generally correspond to an atomic promoter metal oxide:vanadium ratio of from 1:1 to 100:1, wherein the vanadium content is calculated as vanadium pentoxide.

The resulting finally calcined catalyst can be employed as such or deposited (as is preferred) on an inert catalyst carrier such as silicon carbide, silicon nitride, carborundum, steatite, alumina, alundum, and the like.

At some point in their preparation, the catalysts described herein preferably are formed into structures suitable for use in a reactor, although unshaped, powder catalyst can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, Carbowax, Methocel ®, Avicel ® and graphite and the like. Extrusion or pelleting of the catalyst can be achieved by forming a wet paste.

Supported catalysts for use in either fixed or fluidized bed operations employ carriers including alumina, silica, silica gel, silica-alumina, silicon carbide, ceramic donuts, magnesium oxide, titania and titania-silica. Spray dried catalysts can also be employed for fluidized bed operations.

A catalyst support, if used, provides not only the required surface for the catalyst, but gives physical strength and stability to the catalyst material. The carrier or support typically possesses a surface area of from about 0.1 to about 200 m$^2$/g, preferably from about 0.1 to about 50 m$^2$/g, and most preferably from about 0.1 to about 5 m$^2$/g. A desirable form of carrier is one which has a rough enough surface to aid in retaining the catalyst adhered thereto during handling and under reaction conditions. The support may vary in size but generally is from about 2$\frac{1}{2}$ mesh to about 10 mesh in the Tyler Standard screen size. Alundum particles as large as $\frac{1}{4}$ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90% by weight, preferably from about 5 to about 80% by weight based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2$\frac{1}{2}$ to about 10 mesh size. While the supports may be of a variety of shapes, the preferred shape of the supports is in the shape of cylinders or spheres.

The particle size of a supported or unsupported catalyst used in fluidized beds is quite shall, usually varying from about 10 to about 200 microns.

Inert diluents such as silica may be present in the catalyst, but the combined weight of the essential active ingredients of TiO$_2$, vanadium, and reactive metal should preferably consist essentially of at least about 5 wt %, preferably at least about 15 wt %, based on the total weight of catalyst and support.

Shaping of unsupported catalyst can be conducted prior or subsequent to calcination of the V-deposited catalyst precursor. Preferably, shaping of the unsupported catalyst is conducted on the catalyst precursor prior to deposition of V thereon. The point during which shaping with supports or carriers is conducted will vary with the type of support.

Solid supports, such a silica alumina, can be added to the reaction mixture during the formation of the catalyst precursor.

Vapor Phase Oxidation of Hydrocarbons

The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkenes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g., 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene -2 (cis or trans), 3-methylbutene-1, pentene-1, pentene-2, hexene-1, 3,3-dimethylbutene-1, 3-methyl-pentene-2, butadiene, pentadiene, cyclopentadiene, hexadiene, and mixtures thereof. It is also contemplated to use refinery streams rich in alkenes, particularly streams containing 70 percent or more butenes.

Representative examples of cycloalkanes which can be methyl substituted, include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, thiophene can be employed. Also suitable and readily available are naphthas obtained from paraffinic or naphthenic petroleum sources. Full boiling range naphthas (boiling within the range of about 35°-230° C.) can be used but it is preferred to use light naphtha cuts boiling within the range of about 35°-145° C. The naphthas usually contain about 5-15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane or isopentene to citraconic anhydride, maleic anhydride and carboxy maleic anhydride; pseudocumene to trimetallitic anhydride; durene to pyromellitic anhydride; and orthoxylene and naphthalene to phthalic anhydride.

Preparation of Phthalic Anhydride

A preferred hydrocarbon feed for the catalyst of this invention for conversion to phthalic anhydride is orthoxylene, or an aromatic feedstream comprising a predominant amount of orthoxylene and more preferably at least 10 mol. % orthoxylene. In the following discussion and exemplification, therefore, orthoxylene is used in most examples to demonstrate (but not to limit) the use of catalysts made by the process of this invention for producing phthalic anhydride. (It will be understood, for example, that naphthalene can also be employed as a hydrocarbon feed to prepare phthalic anhydride.)

The oxidation of orthoxylene to phthalic anhydride may be accomplished by contacting orthoxylene in low concentrations with oxygen in the presence of the described catalyst. Air is entirely satisfactory as a source of oxygen, but synthetic mixtures of oxygen and diluent gases, such as nitrogen, carbon dioxide and the like also may be employed. Air enriched with oxygen may be employed. The oxygen-containing gas feed (e.g., air) is preferably preheated (e.g., to from 100°–300° C.) before introducing it into the reactor.

The gaseous feedstream to the oxidation reactors normally will contain air and typically from about 0.5 to about 10, preferably from about 1 to about 8, and most preferably from about 1.2 to about 5, mol. % orthoxylene. About 1.0 to about 1.9 mol. % of the orthoxylene in air is satisfactory for optimum yield of product for the process of this invention using a fixed bed reactor, and from about 2.5 to 4.0 mol. % orthoxylene using a fluidized bed. Although higher concentrations may be employed, explosive hazards may be encountered. Lower concentrations of orthoxylene less than about 1%, of course, will reduce the production rate obtained at equivalent flow rates and thus are not normally economically employed.

Flow rates of the gaseous feedstream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained. The hourly loading of the catalyst in a tube having a diameter of 25 mm and a length of 3 meters is generally from about 2000 to 6000 liters of air with about 20 to 150 g. of orthoxylene per 1000 liters of air.

A variety of reactors will be found to be useful and multiple tube heat exchanger type reactors are quite satisfactory. The tubes of such reactors may vary in diameter typically from about 20 to 50 mm, and the length may be varied from about 1 to 5 meters.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon steel, nickel, carbon-glass tubes such as Vycor and the like. Both carbon-steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the orthoxylene concentration. Under usual operating conditions, in compliance with the preferred procedure of this invention, the average bed temperature referred to herein as the reaction temperature, measured by thermocouples disposed in the reactor, is typically from about 300° to about 500° C., preferably from about 320° to about 440° C., and most preferably from about 330° to about 420° C. Under normal conditions, the temperature in the reactor ordinarily should not be allowed to go above about 525° C. for extended lengths of time because of decreased yields and possible deactivation of the novel catalyst of this invention.

The reaction may be conducted at atmospheric, superatmospheric or below atmospheric pressure, with pressure of from 1 to 20 psig being generally entirely suitable.

The phthalic anhydride may be recovered by a number of ways well known to those skilled in the art. For example, the recovery may be by direct condensation or by absorption in suitable media, with subsequent separation and purification of the phthalic anhydride. By-products such as tolualdehyde, phthalide, and maleic anhydride may also be formed, and can be separated from the phthalic anhydride by conventional means. If desired the purified phthalic anhydride can be reacted with an organic alcohol (such as an oxo-alcohol, e.g., isodecyl alcohol) to prepare phthalate esters which find use as plasticizers.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, the reactor used to test the catalyst is described as follows:

The reactor tube for the catalyst bed was fabricated from 316 stainless steel and had a ½-inch outside diameter, a wall thickness of 0.049 inch and a length of 12 inches. The bottom of the reactor tube was charged with 2 cc of 3 mm glass beads (VICOR ® beads), and then about 2 g. of unsupported catalyst, having an average particle size of about 0.5 mm and premixed with about 15 g (8 ml) of 0.55 mm glass beads (VICOR ® beads), was charged to the reactor as the catalyst bed. On top of the catalyst bed was then placed 2 cc of 3 mm glass beads (VICOR ® beads). A ⅛-inch stainless steel thermowell tube was provided down the center of the reactor tube, and a thermocouple was provided within the thermowell for measurement of catalyst bed temperatures along the length of the reactor. The reactor tube was immersed in a HITEC ® salt bath. The reactor inlet pressure as about 1 psig. The orthoxylene feed was caused to pass through the reactor tube in an upflow manner. Once a catalyst evaluation was started the reaction was continued for the longer of the selected run time or 8 hours. At the conclusion of each run, the catalyst, if to be used again, was kept under nitrogen purge at a temperature of from about 320° to 330° C. Analyses of reactor effluent gas were made at convenient time intervals by gas chromatography. Carbon balance was calculated according to the number of gram atoms of carbon in the reactor effluent to the gram atoms of carbon fed to the system.

Conversion of orthoxylene is calculated according to the following equation:

$$\% \text{ o-xylene conversion} = \frac{\text{g-moles of reacted o-xylene}}{\text{g-moles of o-xylene feed}} \times 100$$

Phthalic anhydride yield is calculated according to the following equation:

$$\% \text{ PAN yield} = \frac{\text{g-moles of PAN produced}}{\text{g-moles of o-xylene feed}} \times 100$$

The selectivity of phthalic anhydride is calculated according to the following equation:

$$\% \text{ selectivity to PAN} = \frac{\text{g-moles of PAN produced}}{\text{g-moles of o-xylene reacted}} \times 100$$

(% selectivity to intermediate oxidation products (e.g., tolualdehyde, phthalide) is calculated as shown above.)

In the Examples, the $TiO_2$ (Mobay) anatase charged was determined by atomic absorption analysis to contain about 0.15 wt. % K, 0.10 wt. % P, 0.10 wt. % Al and 0.16 wt. % Si (calculated as the respective elements) all of which are believed to be present as the corresponding metal oxides in the calcined catalysts prepared as described below. All Examples used $TiO_2$ (Mobay), 100% anatase, specific surface area of 9 m²/gm, pore size of 150–250 m; −60+ −200 mesh. All amounts are weight % unless otherwise indicated.

EXAMPLE 1

Preparation of Catalyst

STEP 1 - Catalyst Precursor

Batch A: To about 200 ml of water was added 1.94 grams of vanadium pentoxide, 4.26 grams of oxalic acid and 9.68 grams of formamide at room temperature with stirring to form vanadium oxalate, and this solution was then mixed with 100 grams of titanium dioxide anatase powder (which was first dispersed in 1000 ml of water).

Batch B: To about 400 ml of water was added 3.87 grams of vanadium pentoxide, 8.53 grams of oxalic acid and 19.37 grams of formamide at room temperature with stirring to form vanadium oxalate, and this solution was then mixed with 200 grams of titanium dioxide anatase powder (which was first dispersed in 2000 ml of water).

Batches A and B were each heated with stirring at 65° C to evaporate the majority of the water, followed by drying in an oven (101 kpa) at 110° C. for 16 hours. The resulting catalyst precursor solids were then calcined in a flowing oxygen gas stream at 450° C. for two hours, to form the calcined catlyst precursor. The two batches of catalyst precursor were each treated by crushing and screening to form −20+40 mesh particle size, and were then combined. The calcined catalyst precursor formed by the above impregnation procedure was determined by calculation (based on the vanadium salt and the weight of the titanium dioxide particles) to contain 1.9 wt. % $V_2O_5$ on the $TiO_2$:

STEP 2 - Catalyst

To about 125 ml of water was added vanadium pentoxide, oxalic acid and formamide in the respective gram amounts which are indicated in Table I below for each of Catalysts A through J, at room temperature with stirring to form vanadium oxalate. To prepare each of catalysts A through C and E through J, this solution was then mixed with 25 grams of the powder comprising 1.9 wt. % $V_2O_5$ on titanium dioxide anatase powder prepared in Step 1, and antimony trioxide (which was first dispersed in about 20 ml of water) in the gram amounts also indicated in Table I. (In the preparation of Catalyst D, 15 grams of the powder comprising 1.9 wt. % $V_2O_5$ on titanium dioxide anatase powder prepared in Step 1 were used; but the preparative procedure was otherwise the same.)

The resulting mixtures were each heated with stirring at 65° C. to evaporate the majority of the water followed by drying in an oven (101 kPa) at 110° C. for 16 hours. The solids which formed were then calcined in a flowing oxygen gas stream at 450° C. for 2 hours, followed by crushing and screening to form −20+40 mesh particle size.

Catalysts A through J formed by the above impregnation procedure were determined by calculation (based on the vanadium salt, antimony salt, and the weight of the titanium dioxide particles) to contain antimony and vanadium in the weight percent amounts (based on the oxides thereof) and molar ratios (gram atoms of vanadium to gram atoms of antimony) indicated in Table II below.

Preparation of Phthalic Anhydride

Employing the reactor and process conditions indicated, Catalysts A through J prepared as above were charged to the reactor tube in separate runs to determine their activity for the partial oxidation of orthoxylene to phthalic anhydride. The data thereby obtained for each catalyst are set forth in Table III below.

TABLE I

| Catalyst | $V_2O_5$ (gm) | Formamide (gm) | Oxalic Acid | $Sb_2O_3$ (gm) |
|---|---|---|---|---|
| A | 0.139 | 0.694 | 0.305 | 0.111 |
| B | 0.096 | 1.92 | 0.85 | 0.154 |
| C | 0.423 | 2.12 | 0.93 | 0.452 |
| D | 0.396 | 1.98 | 0.87 | 0.317 |
| E | 1.07 | 5.35 | 2.354 | 0.428 |
| F | 0.576 | 2.88 | 1.27 | 0.924 |
| G | 0.835 | 4.59 | 1.84 | 0.6675 |
| H | 1.468 | 7.34 | 3.23 | 0.785 |
| I | 1.665 | 8.33 | 3.66 | 1.333 |
| J | 2.145 | 10.725 | 4.72 | 0.858 |

TABLE II

| Catalyst | $V_2O_5$ wt. % See fn. 1 | $V_2O_5$ wt. % See fn. 2 | $Sb_2O_3$ wt. % | $V_2O_5/Sb_2O_3$ molar ratio See fn. 3(a) | $V_2O_5/Sb_2O_3$ molar ratio See fn. 4(a) | $(V_2O_5 + Sb_2O_3)$ wt. % See fn. 3(b) | $(V_2O_5 + Sb_2O_3)$ wt. % See fn. 4(b) |
|---|---|---|---|---|---|---|---|
| A | 0.55 | 2.43 | 0.44 | 2.00 | 8.85 | 0.99 | 2.87 |
| B | .38 | 2.26 | 0.61 | 1.00 | 5.94 | 0.99 | 2.87 |
| C | 1.63 | 3.47 | 1.75 | 1.49 | 3.18 | 3.38 | 5.22 |
| D | 2.52 | 4.33 | 2.01 | 2.01 | 3.45 | 4.53 | 6.34 |
| E | 4.04 | 5.83 | 1.61 | 4.02 | 5.80 | 5.65 | 7.44 |
| F | 2.17 | 3.96 | 3.49 | 1.00 | 1.82 | 5.66 | 7.45 |
| G | 3.15 | 4.94 | 2.52 | 2.00 | 3.14 | 5.65 | 7.46 |
| H | 5.39 | 7.13 | 2.88 | 3.00 | 3.97 | 8.27 | 10.01 |

TABLE II-continued

| Catalyst | V$_2$O$_5$ wt. % See fn. 1 | V$_2$O$_5$ wt. % See fn. 2 | Sb$_2$O$_3$ wt. % | V$_2$O$_5$/Sb$_2$O$_3$ molar ratio See fn. 3(a) | V$_2$O$_5$/Sb$_2$O$_3$ molar ratio See fn. 4(a) | (V$_2$O$_5$ + Sb$_2$O$_3$) wt. % See fn. 3(b) | (V$_2$O$_5$ + Sb$_2$O$_3$) wt. % See fn. 4(b) |
|---|---|---|---|---|---|---|---|
| I | 5.95 | 7.65 | 4.76 | 2.00 | 2.58 | 10.71 | 12.41 |
| J | 7.66 | 9.36 | 3.06 | 4.01 | 4.90 | 10.72 | 12.42 |

1 Weight percent, based on total catalyst weight, of V$_2$O$_5$ co-deposited with the reactive metal oxide on the calcined catalyst precursor (excluding the 1.9 wt. % V$_2$O$_5$ in the catalyst precursor).
2 Weight percent, based on total catalyst weight, of total V$_2$O$_5$ in the catalyst (including the 1.9 wt. % V$_2$O$_5$ present in the catalyst precursor).
3(a) Molar ratio of V$_2$O$_5$ to Sb$_2$O$_3$ co-deposited on the calcined catalyst precursor (excluding the V$_2$O$_5$ in the catalyst precursor).
(b) Combined weight percent, based on total catalyst weight, of V$_2$O$_5$ and Sb$_2$O$_3$ co-deposited on the calcined catalyst precursor (excluding the V$_2$O$_5$ in the catalyst precursor).
4(a) Molar ratio of V$_2$O$_5$ to Sb$_2$O$_3$ in the catalyst (including the V$_2$O$_5$ in the catalyst precursor).
(b) Combined weight percent, based on total catalyst weight, of V$_2$O$_5$ and Sb$_2$O$_3$ present in the catalyst (including the V$_2$O$_5$ present in the catalyst precursor).

TABLE III

| Catalyst | Temp. (°C.) | Run[1] Time (hrs) | o-xylene Conversion (mol %) | PAN Yield (mol %) | PAN Yield (wt. %) | Selectivities (mol %) to: PAN | Tol | Ph |
|---|---|---|---|---|---|---|---|---|
| Catalyst A | 337 | 3.0 | 100 | 74.7 | 104.2 | 74.7 | 0.0 | 0.0 |
| Comparative | 332 | 3.1 | 99.6 | 76.5 | 106.7 | 76.8 | 0.0 | 0.0 |
|  | 326 | 4.0 | 95.1 | 75.0 | 104.7 | 78.9 | 0.2 | 0.0 |
| Catalyst B | 342 | 3.1 | 100 | 68.1 | 95.0 | 68.1 | 0.0 | 0.0 |
| Comparative | 337 | 2.0 | 97.0 | 70.1 | 97.8 | 72.3 | 0.2 | 0.0 |
|  | 332 | 2.8 | 88.1 | 67.7 | 94.5 | 76.9 | 0.3 | 0.0 |
| Catalyst C | 332 | 2.6 | 100 | 80.6 | 112.4 | 80.6 | 0.0 | 0.0 |
|  | 329 | 2.7 | 96.5 | 77.9 | 108.6 | 80.7 | 0.5 | 0.0 |
|  | 325 | 3.0 | 85.8 | 70.9 | 99.9 | 82.6 | 1.0 | 0.0 |
| Catalyst D | 331 | 6.0 | 100 | 100 | 115.5 | 82.8 | 0.0 | 0.0 |
|  | 328 | 4.0 | 99.8 | 82.8 | 115.6 | 83.0 | 0.0 | 0.0 |
| Catalyst E | 334 | 3.0 | 100 | 82.7 | 115.4 | 82.7 | 0.0 | 0.0 |
|  | 328 | 2.5 | 87.4 | 70.5 | 99.4 | 80.7 | 2.3 | 1.7 |
|  | 322 | 2.6 | 66.1 | 50.8 | 70.9 | 76.9 | 3.9 | 3.2 |
| Catalyst F | 335 | 3.2 | 100 | 82.5 | 115.1 | 82.1 | 0.0 | 0.0 |
|  | 331 | 2.8 | 97.4 | 80.5 | 112.4 | 82.7 | 0.4 | 0.0 |
|  | 325 | 2.7 | 79.1 | 65.1 | 90.8 | 82.3 | 2.0 | 1.2 |
| Catalyst G | 334 | 2.4 | 100 | 83.2 | 116.1 | 83.2 | 0.0 | 0.0 |
|  | 328 | 2.6 | 90.0 | 74.3 | 103.7 | 82.6 | 1.3 | 0.0 |
|  | 323 | 2.5 | 70.3 | 55.9 | 78.0 | 79.5 | 3.2 | 1.6 |
|  | 317 | 2.9 | 51.6 | 37.9 | 52.9 | 73.5 | 7.2 | 3.0 |
|  | 330 | 2.1 | 95.9 | 79.3 | 110.6 | 82.7 | 0.8 | 0.0 |
|  | 332 | 3.0 | 98.8 | 81.6 | 113.8 | 82.6 | 0.3 | 0.0 |
| Catalyst H | 335 | 3.0 | 100.0 | 80.6 | 112.4 | 80.6 | 0.0 | 0.0 |
|  | 333 | 2.5 | 98.3 | 78.3 | 110.7 | 80.7 | 0.2 | 0.0 |
|  | 329 | 2.8 | 90.3 | 72.2 | 100.8 | 80.0 | 1.2 | 0.0 |
|  | 323 | 2.8 | 69.3 | 54.1 | 75.5 | 78.1 | 3.1 | 1.5 |
|  | 317 | 2.3 | 51.6 | 37.9 | 52.9 | 73.5 | 5.1 | 2.4 |
| Catalyst I | 341 | 3.0 | 99.8 | 80.0 | 111.7 | 80.2 | 0.0 | 0.0 |
| Comparative | 336 | 2.6 | 97.2 | 78.5 | 109.6 | 80.8 | 0.2 | 0.0 |
|  | 329 | 2.6 | 88.2 | 71.6 | 99.9 | 81.2 | 1.0 | 0.0 |
|  | 337 | 3.7 | 99.2 | 79.6 | 111.0 | 80.2 | 0.0 | 0.0 |
|  | 329 | 2.6 | 89.8 | 72.3 | 100.8 | 80.5 | 0.9 | 0.0 |
|  | 323 | 2.9 | 69.2 | 55.3 | 77.1 | 79.9 | 2.6 | 0.0 |
|  | 317 | 2.6 | 50.4 | 37.8 | 52.7 | 75.0 | 4.5 | 1.8 |
| Catalyst J | 336 | 3.5 | 100 | 79.1 | 110.3 | 79.1 | 0.0 | 0.0 |
| Comparative | 329 | 2.4 | 94.5 | 74.8 | 104.4 | 79.2 | 0.7 | 0.0 |
|  | 324 | 2.7 | 71.9 | 55.6 | 77.5 | 77.3 | 2.8 | 1.4 |
|  | 333 | 2.7 | 100 | 79.1 | 110.3 | 79.1 | 0.0 | 0.0 |
|  | 331 | 1.7 | 98.6 | 78.6 | 109.6 | 79.7 | 0.2 | 0.0 |

Notes
"PAN" - phthalic anhydride;
"Tol" - tolualdehyde;
"Ph" - phthalide
[1] vapor feed to reactor = 1.25 mol % o-xylene in air; space velocity = 2760 hr$^{-1}$.

What is claimed is:

1. A process for the preparation of a carboxylic anhydride comprising reacting a hydrocarbon with molecular oxygen in the vapor phase, in the presence of a solid oxidation catalyst, said solid oxidation catalyst being obtained by the steps of:

(a) forming a catalyst precursor by depositing on a titanium dioxide support in the anatase form, at least a monolayer amount of at least one vanadium oxide source which is convertible to vanadium oxide upon calcining;

(b) calcining said catalyst precursor under conditions sufficient to convert at least a portion of said vanadium oxide source into vanadium oxide;

(c) depositing upon the calcined catalyst precursor a catalytically effective amount of at least one vanadium oxide source which is convertible to vanadium oxide upon calcining and at least one reactive metal source selected from the group consisting of compounds of Sb, Ga, Ge, In, Tl, Pb, Bi, P, Te and Se which are convertible to the corresponding metal oxide upon calcining, said canadium oxide source and said reactive metal oxide source being deposited in amounts sufficient to provide a molar ratio of vanadium to the reactive metal of at least about 1:1 up to about 4:1 gram atom or vanadium per gram atom of reactive metal, and wherein the combined weight percent of vanadium and reactive metal thus deposited (based on the oxides thereof) is from about 4 to about 6 wt. %, based on total catalyst weight; and (d) calcining the catalyst solids formed in step (c) under conditions sufficient to convert at least a portion of said vanadium and metal oxide compounds to vanadium and the reactive metal oxide, the catalyst thereby formed comprising vanadium and the reactive metal in a molar ratio of at least about 1:1 gram atom up to about 6:1 of vanadium per gram atom of reactive metal, and wherein the combined weight percent of vanadium and the reactive metal (based on the oxides thereof) is about 6 to about 8 wt. %, based on total catalyst weight.

2. The process according to claim 1 wherein said catalyst precursor is calcined in step (b) at a temperature of from about 150° to 750° C.

3. The process according to claim 2 wherein said calcining is effected for a time of from about 0.5 to 16 hours.

4. The process according to claim 1 wherein said vanadium source comprises at least one member selected from the group consisting of vanadium halides, phosphates, oxides, carbonates, sulfates, alkoxides, nitrates, hydroxides, carboxylates and oxy halides.

5. The process according to claim 4 wherein said vanadium source comprises at least one compound selected from the group consisting of vanadium pentoxide, ammonium metavanadate, vanadyl sulfate, vanadyl chloride, vanadyl dichloride, metavanatic acid, pyrovanatic acid, vanadium hydroxide, vanadyl oxalate and vanadyl carboxylate.

6. The process according to claim 1 wherein said catalyst, following calcination according to step (d), is characterized by specific surface area of less than 50 square meters per gram.

7. The process according to claim 1 wherein said hydrocarbon comprises at least one member selected from the group consisting of orthoxylene and naphthalene, and wherein said carboxylic anhydride comprises phthalic anhydride.

8. The process according to claim 7 wherein said orthoxylene or naphthalene feed is passed to a reaction zone containing said solid oxidation catalyst at a mass flow rate of from about 20 to 150 grams per $Nm^3$ under vapor phase conditions, said reaction being effected at a temperature of from about 200° to 500° C.

9. The process according to claim 7 wherein said hydrocarbon comprises durene and wherein said carboxylic anhydride comprises pyromellitic dianhydride.

10. The process according to claim 9 wherein said durene is passed to a reaction zone containing said solid oxidation catalyst under vapor phase reaction conditions and at a durene feed rate of from about 5 to 100 grams per $Nm^3$, and said reaction is effected at a temperature within the range of from about 2000° to 500° C.

11. The process according to claim 1 wherein said vanadium oxide source is deposited on said titanium dioxide in step (a) in an amount sufficient to provide at least $N_{min}$ grams of $V_2O_5$ per gram of said titanium dioxide, wherein $$N_{min} = (G) \times (A) \times (0.0007)$$

wherein "G" is the grams of said titanium dioxide and "A" is the specific surface area of said titanium dioxide.

12. The process according to claim 11 wherein said vanadium oxide source is deposited on said titanium dioxide in an amount sufficient to provide an amount of $V_2O_5$ of from $1(N_{min})$ to 40 ($N_{min}$) wherein $N_{min}$ is as previously defined.

13. A process for the preparation of a carboxylic anhydride comprising reacting a hydrocarbon with molecular oxygen in the vapor phase in the presence of a solid oxidation catalyst, said solid oxidation catalyst being obtained by the steps of:

(a) forming a catalyst precursor by depositing on a titanium dioxide support in the anatase form, at least one vanadium oxide source which is convertible to vanadium oxide upon calcining, said vanadium oxide source being deposited on said titanium dioxide in an amount sufficient to provide at least $N_{min}$ grams of $V_2O_5$ per gram of said titanium dioxide support, wherein $$N_{min} = (G) \times (A)(0.0007)$$

wherein "G" is the grams of said titanium dioxide and "A" is the specific surface area of said titanium dioxide;

(b) calcining said catalyst precursor under conditions sufficient to convert at least a portion of said vanadium oxide source into vanadium oxide;

(c) depositing upon the calcined catalyst precursor of at least one vanadium oxide source which is convertible to vanadium oxide upon calcining and at least one reactive metal source selected from the group consisting of compounds of Sb, GA, Ge, In, Tl, Pb, Bi, P, Te and Se which are convertible to the corresponding metal oxide upon calcining, said vanadium oxide source and said reactive metal oxide source being deposited in amounts sufficient to provide a molar ratio of vanadium to the reactive metal of from about 1:1 to about 4:1 gram atom of vanadium per gram atom of reactive metal, and wherein the combined weight percent of vanadium and reactive metal thus deposited (based on the oxides thereof) is from about 4 to about 6 wt. %, based on total catalyst weight; and (d) calcining the catalyst solids formed in step (c) under conditions sufficient to convert at least a portion of said vanadium and metal oxide compounds to vanadium and the reactive metal oxide, the catalyst thereby formed comprising vanadium and the reactive metal in a molar ratio of about 1:1 to about 6:1 gram atom of vanadium per gram atom of reactive metal, and wherein the combined weight percent of vanadium and the reactive metal (based on the oxides thereof) is about 6 to about 8 wt. %, based on total catalyst weight.

14. The process according to claim 13 wherein said vanadium oxide source is deposited on said titanium dioxide in an amount sufficient to provide an amount of $V_2O_5$ of from $1(N_{min})$ to $40(N_{min})$.

15. The process according to claim 14 wherein said vanadium source comprises at least one compound selected from the group consisting of vanadium pentoxide, ammonium metavanadate, vanadyl sulfate, vanadyl chloride, vanadyl dichloride, metavanatic acid, pyrovanatic acid, vanadium hydroxide, vanadyl oxylate, and vanadyl carboxylate.

16. The process according to claim 15 wherein said catalyst, following calcination according to step (d), is characterized by specific surface area of less than 50 square meters per gram.

17. The process according to claim 16 wherein said hydrocarbon comprises at least one member selected from the group consisting of orthoxylene and naphthalene, and wherein said carboxylic anhydride comprises phthalic anhydride.

18. The process according to claim 17 wherein ortho-xylene or napthalene feed is passed to a reaction zone containing said solid oxidation catalyst under vapor phase reaction conditions and at a mass flow rate of from about 20 to 150 grams per $N^3$, and said reaction is effected at a temperature of from about 200° to 500° C.

19. The process of claim 1 wherein the vanadium source is vanadium pentoxide, the reactive metal oxide is $Sb_2O_3$, the carboxylic anhydride is phthalic anhydride and the hydrocarbon is o-xylene.

20. The process of claim 19 wherein the weight % yield of phthalic anhydride is about 115%.

21. The process of claim 19 wherein the weight % of yield of phthalic anhydride is about 116%.

* * * * *

UNITED STATES PATENT AND TRADEMARK OFFICE
CERTIFICATE OF CORRECTION

PATENT NO. : 4,855,457
DATED : August 8, 1989
INVENTOR(S) : Ramzi Y. Saleh, Israel E. Wachs It is certified that error appears in the above—identified patent and that said Letters Patent is hereby corrected as shown below:

On the Title page, starting at line 8 of the Abstract, please amend as follows:

b) calcining the thus formed catalyst precursor under conditions sufficient to convert the [tantalum oxide source] vanadium oxide source.

Signed and Sealed this

Twenty-eighth Day of August, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,855,457

DATED : August 8, 1989

INVENTOR(S) : Ramzi Y. Saleh, Israel E. Wachs

It is certified that error appears in the above—identified patent and that said Letters Patent is hereby corrected as shown below:

On the Title page, at the line listing Inventors, please delete "Saleh Y. Ramzi" and insert therefore --Ramzi Y. Saleh--.

Signed and Sealed this

Seventh Day of May, 1991

*Attest:*

HARRY F. MANBECK, JR.

*Attesting Officer*     *Commissioner of Patents and Trademarks*